US010905139B2

(12) United States Patent
Coy

(10) Patent No.: US 10,905,139 B2
(45) Date of Patent: Feb. 2, 2021

(54) REFRESHING BEVERAGE

(71) Applicant: Johannes Coy, Hainburg (DE)

(72) Inventor: Johannes Coy, Hainburg (DE)

(*) Notice: Subject to any disclaimer, the term of this patent is extended or adjusted under 35 U.S.C. 154(b) by 0 days.

(21) Appl. No.: 16/188,384

(22) Filed: Nov. 13, 2018

(65) Prior Publication Data
US 2019/0142035 A1 May 16, 2019

Related U.S. Application Data

(62) Division of application No. 13/978,535, filed as application No. PCT/DE2011/002144 on Dec. 20, 2011, now Pat. No. 10,143,221.

(30) Foreign Application Priority Data

Jan. 6, 2011 (DE) .................. 10 2011 008 017

(51) Int. Cl.
| A23L 2/52 | (2006.01) |
| A23L 2/60 | (2006.01) |
| A23L 2/68 | (2006.01) |
| A61K 31/191 | (2006.01) |
| A61K 31/7016 | (2006.01) |
| A61K 36/73 | (2006.01) |
| A61K 36/736 | (2006.01) |
| A61K 36/752 | (2006.01) |

(52) U.S. Cl.
CPC ............... *A23L 2/52* (2013.01); *A23L 2/60* (2013.01); *A23L 2/68* (2013.01); *A61K 31/191* (2013.01); *A61K 31/7016* (2013.01); *A61K 36/73* (2013.01); *A61K 36/736* (2013.01); *A61K 36/752* (2013.01)

(58) Field of Classification Search
CPC ........................................................ A23L 2/52
See application file for complete search history.

(56) References Cited

U.S. PATENT DOCUMENTS

| 7,098,193 B2 | 8/2006 | Myatt et al. |
| 2001/0022980 A1 | 9/2001 | Bell et al. |
| 2002/0132780 A1 | 9/2002 | Heisey et al. |
| 2007/0116822 A1 | 5/2007 | Prakash et al. |
| 2007/0116833 A1 | 5/2007 | Prakash et al. |
| 2008/0171032 A1 | 7/2008 | Kelly |
| 2008/0292765 A1 | 11/2008 | Prakash et al. |

FOREIGN PATENT DOCUMENTS

| DE | 3811964 A1 | 10/1989 | |
| DE | 102008050591 A1 | 4/2010 | |
| JP | H07277991 A | 10/1995 | |
| KR | 1020050011834 A | 1/2005 | |
| WO | 2008112857 A1 | 9/2008 | |
| WO | 2009153064 A2 | 12/2009 | |
| WO | WO-2009153064 A2 * | 12/2009 | ............... A23L 2/52 |

OTHER PUBLICATIONS

Sortwell: Drinks that won't decay: beverage formulation for oral health: In: Food & Beverage, Asia. Dec. 2004. pp. 32-34.
Wells, JW. "Practical Bottling". From "The Beverage Journal" (Jan. 1922), p. 9.
Yaping et al. Nutrition Research, Nov. 2003, vol. 23, Issue 11, pp. 1591-1595 (abstract only).

* cited by examiner

*Primary Examiner* — Amy L Clark
(74) *Attorney, Agent, or Firm* — Agris & Von Natzmer, LLP; Joyce Von Natzmer

(57) ABSTRACT

Disclosed is a beverage and a method of administering the beverage. The beverage is free of phosphoric acid and instead contains at least 0.3% by weight/volume of gluconic acid, is low in minerals, specifically contains less than 250 mg/liter of minerals, is low in sugar, specifically contains at most 2.5% by weight/volume of sugar. These sugars comprise at least 10% weight/weight galactose and in addition a proportion of isomaltulose and/or tagatose The beverage has a glycemic index of at most 35 (GI<35).

20 Claims, No Drawings

REFRESHING BEVERAGE

CROSS-REFERENCE TO RELATED APPLICATIONS

This is a divisional application of U.S. application Ser. No. 13/978,535, now U.S. Pat. No. 10,143,221, which is the U.S. national stage of International application PCT/DE2011/002144, filed Dec. 20, 2011 designating the United States and claiming priority to DE 102011008017.1, filed Jan. 6, 2011.

The invention relates to a novel sweet-tasting refreshing beverage that is free from phosphoric acid, is low in minerals and is low in sugar.

The feeling of being thirsty is produced either when there is a lack of fluid in the body or when there is an excess of salt (mineral excess). By taking on fluid, the lack of fluid or the mineral excess in the body can be counterbalanced, provided the fluid is free from minerals or low in minerals. A high mineral content of the fluid, as in the case of seawater, can, by contrast, lead to the paradoxical situation that a person dies of thirst in spite of fluid intake because the high mineral content in the seawater no longer enables net removal of minerals from the body. In spite of drinking, the mineral excess in the body rises further, until death ultimately occurs. A drinking fluid should therefore contain few minerals unless a rise in the mineral content in the body is desired.

The population of western developed nations largely has a lifestyle with relatively little physical movement. Situations in which the body perspires and a high mineral loss consequently occurs are usually the exception in the case of individuals forming these population groups. It is therefore precisely these individuals who should satisfy their daily fluid need primarily or completely with beverages that are low in minerals.

The conventional beverage consumption of individuals in western developed nations leads in many individuals and in particular in many children to an oversupply of the human body with sugar in the form of glucose and fructose due to the excessive supply of sweet beverages. Most commercially available conventional beverages have a relatively high content of sucrose (cane sugar), a disaccharide formed from glucose and fructose. Sucrose has a high glycemic index, that is to say the intake of sucrose in the body leads to a rapid and sharp rise of the blood sugar level and, consequently, also to a sharp rise of the insulin level in the blood.

The consumption of beverages rich in sucrose (sugar content more than 4 wt/vol %) leads to a particularly rapid and high blood sugar rise and therefore results in a very high insulin discharge. In accordance with the principle of negative feedback, the effect of the insulin in turn leads to a fall in the blood sugar level, and, in the case of a high insulin level, this fall occurs in a correspondingly drastic manner. The drastic fall in the blood sugar level then in turn leads to a drop in performance and poorer concentration and triggers the feeling in the brain of a ravenous appetite for sweet things in order to again raise the blood sugar level as a result of an intake of sugars. The consumer concerned consequently finds himself in a vicious cycle that induces him to continually consume beverages that are rich in sugar and are therefore high in calories.

In addition, sugars with a high glycemic index have to, or should, be avoided in particular by patients suffering from type 2 diabetes and by patients suffering from cancer.

The current increase in the incidence of type 2 diabetes underlines the need to provide foodstuffs, including beverages, that have a relatively low glycemic index (GI) and a relatively low glycemic load (GL) and therefore cause only a relatively low insulin output. Cancer occurs more frequently in diabetics than in the average population. The currently high carbohydrate intake in the population of western developed nations and the increasing consumption of carbohydrate in countries such as India and China lead not only to an ever-increasing incidence of diabetes, but also of cancer.

Cancer is a multi-stage process, which, from a healthy cell, leads via a benign tumor cell to the formation of a malignant tumor cell (cancer cell). Triggers of this process include gene changes (mutations), which change the growth and mortality properties of a cell, such that said cell divides and therefore multiplies, without this being of use to the organism as a whole. As a result of the increased cell multiplication and the reduced mortality of the cells, a cell collection/cell cluster is initially produced and is referred to as a benign tumor. The benign tumor displaces the healthy surrounding tissue, without destroying it or growing into it (non-invasive growth). The benign tumors may develop into malignant tumors if their metabolism changes, specifically if they change over from burning metabolism to fermentation metabolism, more specifically even in the presence of oxygen (aerobic glycolysis or Warburg effect). A number of influences are known that trigger this changeover: oxygen shortage in relatively large tumors or in tumors having a poor supply of blood, radical loading of the tumor cell as a result of chronic inflammation, chemotherapies and radiation therapies, and anti-angiogenesis active ingredients. The lactic acid formed during fermentation metabolism destroys the surrounding tissue, such that the tumor can grow into said tissue (invasive growth), and it inhibits the attack of the immune system. The cells then growing invasively can spread in the entire body via the lymph vessel and blood vessel system and can form distance metastases (spread). Due to the interruption of the burning metabolism in the mitochondria (oxidative phosphorylation), the formation of radicals and the triggering of apoptosis are suppressed, and these cancer cells are hereby also resistant to radiation therapies and chemotherapies.

Increased consumption of easily digestible carbohydrates (in particular in the form of sugars and starch with a high glycemic index) promotes the transition of tumor cells into cancer cells, accompanied by a rise in activity of the gene TKTL1 (transketolase-like-1 gene). The TKTL1 gene products cause an oxygen-independent release of energy, which leads to no radical formation and neutralizes present or exogenously induced radicals. At the same time, the activity of the mitochondria is reduced and apoptosis (programmed cell death) is inhibited. In accordance with the current state of science, increased activity of the TKTL1 gene is causal or at least a significant reason for the production of aggressive cancer diseases.

With the evidence of the activity of the TKTL1 gene in tumor cells (for example directly in tumor cells or indirectly by evidence of the TKTL1 protein in bodily fluids or in phagocytes/macrophages), cancer patients can be identified whose illness can be mitigated or even cured by means of dietetic therapy with restriction of the carbohydrate quantity and use of sugar forms with a low glycemic index because the growth of TKTL1-positive tumors and metastases is inhibited as a result of the reduced carbohydrate and in particular glucose supply.

Since the sugar uptake in cancer cells is often also facilitated with the aid of insulin and since insulin additionally exerts a growth-promoting effect, even on cancer cells, it is in principle desirable to induce just a low insulin output after the consumption of a meal.

Besides the described sweet beverages, which contain cane sugar/sucrose as a sugar component, there are also those in which the sugar component is provided completely or for the most part in the form of sugar alcohols, artificial sweeteners, fructose, isomaltulose, or combinations thereof. For example, in what are known as diabetic beverages, either sugar alcohols (for example polyols) or fructose or artificial sweeteners or combinations thereof are used instead of sucrose.

The sugar alcohols have a low glycemic index, but can lead to health problems because they cannot be digested completely by human enzymes and are broken down in part via the intestinal flora, which often leads to gas formation, bloating and diarrhea.

Artificial sweeteners likewise have a low glycemic index, however severe health-damaging side effects have become known in the meantime for many of them. In the case of aspartame, it has been proven that, after relatively long periods of storage or after storage in a warm environment, it transitions into the alcohol methanol, which can convert into formaldehyde and formic acid, which are two carcinogenic substances. The artificial sweetener saccharin has been proven both in human medical research and in veterinary medical research to be a contributor of bladder cancer, although in veterinary medicine it has also been associated with other forms of cancer.

Fructose has a low glycemic index. In human nutrition, fructose particularly has the disadvantage compared to glucose however that approximately 30-40% of the population in the western world suffers from fructose malabsorption. In addition, fructose, in contrast to glucose, is only transported in an uncontrolled manner from the intestine into the cells, merely due to its concentration gradient. With high fructose quantities in food, health problems such as osmotic diarrhea, serotonin deficiency (as a result of chemical reactions of fructose with tryptophan in the intestine) or increased uric acid production (as a result of increased fructose-1-phosphate formation in the liver) may therefore occur.

Isomaltulose is a sugar occurring in honey and sugar cane and can be produced from sucrose. Similarly to sucrose, isomaltulose consists of the two monosaccharides glucose and fructose, but has a similar, although reduced, sweet profile. Due to a more stable molecular bond between the glucose and fructose molecule compared to sucrose, isomaltulose is cleaved more slowly by the human disaccharidases in the small intestine compared to sucrose, and the blood glucose rise and insulin rise therefore also occur more slowly. At GI=32, the glycemic index of isomaltulose is much lower than that of sucrose (GI=65).

In some conventional beverages, phosphoric acid is contained in order to produce a pleasant, slightly acidic taste. Phosphoric acid attacks the teeth however, and the phosphorous contained in phosphoric acid impairs the uptake of calcium in the body, which may lead to a weakening of the bones. For the Framingham osteoporosis study, Tucker and her colleagues carried out tests on more than 2,500 women aged below 60. For this purpose, they took bone density measurements at the spinal column and three different hip regions and determined that the bone density in women who regularly drank cola had reduced by 4% in all three hip regions, irrespective of how old they were, whether they were going through the menopause, were taking additional calcium or vitamin D preparations or were consuming alcohol or were smokers. ("Colas, but not other carbonated beverages, are associated with low bone mineral density in older women: The Framingham Osteoporosis Study" American Journal of Clinical Nutrition, Vol. 84, No. 4, 936-942, October 2006).

The object of the present invention is therefore to provide a beverage that is free from phosphoric acid, is low in minerals and is low in sugar, yet is still sweet-tasting and has a low glycemic index, that is suitable for counterbalancing a lack of fluid in the body without at the same time supplying high quantities of minerals to the body, and that satisfies the indulgent need for sweet and refreshing beverages without at the same time supplying harmful acids and sugars to the body in a form which causes a sharp rise in the insulin concentration in the blood and which, in the most negative case, can lead to insulin-induced hypoglycemia and to a lack of energy after consumption of the beverage.

A solution to this problem lies in a sweet-tasting refreshing beverage that is free from phosphoric acid, is low in minerals and is low in sugar, and that is characterized in that
it has a content of gluconic acid that is at least 0.3 wt/vol %,
in that any content of minerals is less than 250 mg/liter (0.025 wt/vol %), preferably less than 150 mg of minerals per 1 liter (0.015 wt/vol %) and particularly preferably less than 100 mg of minerals per 1 liter (0.01 wt/vol %),
the content of sugars is at most 2.5 wt/vol % and comprises a fraction of galactose that is at least 10 weight-weight % based on the content of sugars and comprises a fraction of isomaltulose and/or tagatose and/or trehalose and/or ribose,
and in that the beverage has a glycemic index of at most 35 (GI<35).

With this refreshing beverage, it is possible for the first time to satisfy the body's need for fluid without disturbing the existing mineral balance whilst simultaneously satisfying the need for a sweet-tasting refreshing beverage without altering the existing blood sugar level in such a way that there is a rise of the insulin concentration in the blood, and without exposing the teeth to a tooth-damaging medium, and all this without the use of health-damaging ingredients and without the use of artificial sweeteners, artificial colorants and artificial flavorings.

In addition, in particular for individuals who do not partake in much physical exercise, but perform mentally challenging work and have to summon high levels of concentration, the beverage according to the invention provides the advantage that the contained galactose supplies the nerve cells with the necessary energy, even if the glucose level in the blood is low. Even for individuals with insulin resistance, this property of the beverage is of particular advantage.

The beverage is therefore also very well suited in accordance with the invention as a foodstuff or dietary supplement in the preventative or therapeutic treatment of illnesses from the group comprising: celiac disease, type 2 diabetes mellitus, neurodegenerative diseases, in particular Alzheimer's disease, tumors, and illnesses that lead to cachexia (wasting syndrome), which accompany inflammatory processes or are caused thereby, in particular rheumatism, rheumatoid arthritis, inflammatory intestinal diseases such as ulcerative colitis and crohn's disease, and intestinal diseases such as leaky-gut syndrome (bowel hyperpermeability).

With the use according to the invention, individuals who are affected either by one of the aforementioned illnesses or who are at risk of developing such diseases, either genetically or as a result of diet, can receive therapeutic or preventative treatment.

Unless stated otherwise, the following definitions apply in the present description and claims:

- Refreshing beverage=beverage that contains water (drinking water and/or natural mineral water and/or spring water and/or table water) and flavor-imparting ingredients, and in addition may contain further additives, for example carbon dioxide, mineral substances, vitamins, types of sugar, fruit juices and/or fruit concentrates, and flavoring agents (see also the German Food Act, Guidelines for Refreshing Beverages, version as of 18 Mar. 2003; Joint Ministerial Journal (GMB1.) no. 18, p. 383).
- Sugar=sweet-tasting mono- di- and trisaccharides, such as sucrose, glucose, lactose, galactose, fructose, invert sugar, isomaltulose, maltose, melezitose, tagatose, trehalose, and ribose.
- Sugar alcohols (synonym: alditols)=non-cyclic polyols, which are derived structurally by reduction of sugars, such as sorbitol, xylitol, mannitol, maltitol, isomaltol, and erythritol.
- Caramel coloring=foodstuff dye with a sweet to slightly bitter flavor, which is produced from sugars, preferably from sugars with a low glycemic index, such as isomaltulose, by heating to 120 to 150° C. and without additives of health-damaging reaction accelerators.
- Minerals=sum of the dissolved mineral components, in particular magnesium and calcium, but also sodium, sulfate, potassium, silicic acid, chloride and fluoride, except for hydrogen carbonate and dissolved carbon dioxide.
- Content of tocotrienols=the content of alpha- and/or beta- and/or gamma- and/or delta-tocotrienol.
- Low in sugar=no more than 2.5 g of sugar per 100 ml of fluid (in accordance with the revision of (EC) Regulation no. 1924/2006 of the European Parliament and of the Council of 20 Dec. 2006 concerning nutritional value and health-based specifications of foodstuffs—Official Journal of the European Union L 12 of 18 Jan. 2007).
- Low in minerals=low content of minerals in accordance with German "Mineral Water and Table Water Regulation of 1 Aug. 1984—Official Journal (BGB1.) I p. 1036, last amended by Article 1 of the Regulation of 1 Dec. 2006—Official Journal (BGB1.) I p. 2762, last amended by Article 1 of the Regulation of Jan. 12, 2006—Official Journal (BGB1.) I p. 2762). The mineral substance content calculated as solid residue is no more than 500 mg/l of fluid.

Galactose is a sugar that, as a component of milk sugar (lactose), is a natural component of the human diet. Besides glucose and fructose, galactose belongs to those monosaccharides that are consumed most frequently by humans and are therefore supplied most frequently to the human metabolism. Galactose, as a component of carbohydrates, is required in various mucous membranes (anabolic reactions) and, as required, can also be used for catabolic reactions once converted to glucose.

In contrast to glucose, galactose is transported in the human body into the cells independently of insulin. The glycemic index (GI) of galactose at GI=20 is very low compared to sucrose (GI=65) and glucose (GI=100). By contrast, the sweetness of galactose is at least half as much as that of glucose or sucrose: based on sucrose, a 10% D-galactose solution has a sweetness of 63%.

Due to its suitability as a catabolic substrate, that is to say as a supplier of energy, galactose is particularly advantageous for patients who have an insulin resistance and in which there is an undersupply to the glucose-dependent nerve cells, in particular of the brain, in spite of a high blood sugar level—for example in patients suffering from Alzheimer's disease. By administering galactose or galactose-containing foodstuffs, such patients can be supplied with glucose indirectly in a manner independent of insulin (galactose is channeled into the nerve and brain cells in a manner independent of insulin via GluT-3 transporters, where it is converted into glucose). In principle, the intake of galactose in a healthy person also leads, at least in the long term, to higher muscular and cognitive ability.

Galactose itself causes only a relatively low insulin discharge, and thus promotes energy production by means of fat-burning indirectly, that is to say via the relatively low insulin level. In addition, hypoglycemic states and ravenous hunger attacks caused thereby are avoided as a result of the low insulin output. Galactose is therefore very well suited as a sugar component in the diet of individuals who have to control their weight or who have to lose excess weight.

In contrast to glucose and fructose, galactose occurs in nature only in small amounts as a monosaccharide. Galactose is conventionally consumed by humans almost exclusively in the form of the disaccharide lactose. Many adults however have a deficiency of the enzyme lactase, which cleaves lactose, and therefore suffer from lactose intolerance. For this reason, the foodstuff industry is increasingly dispensing with the use of lactose in foodstuffs. The fraction of galactose in the human diet is therefore also reduced.

Although galactose in the form of the free monosaccharide is digestible for humans with lactase deficiency, and although highly pure galactose is available in the prior art, the monosaccharide galactose has not previously been used in beverages. One reason for this could lie in the fact that galactose is suspected of promoting radical formation in the cell and of triggering mitochondria dysfunction.

On the other hand, tests carried out by the Nobel prize-winner Otto Heinrich Warburg have shown that the fermentation metabolism of cancer cells (in cancer tissue sections) progresses most effectively with glucose as a food substrate, specifically at a rate of 23.9 consumed units per unit of time, whereas, with the substrate fructose, it progresses less effectively by a factor of 7 (rate 3.3), and, with galactose, progresses even less effectively by a factor of 18 (rate 1.3). This means: cancer cells provided only with galactose as a food substrate have a comparatively drastically reduced fermentation metabolism and as a result a correspondingly reduced growth rate and division rate. Galactose should therefore be a key sugar source in the diet of cancer patients.

Besides its low glycemic index, isomaltulose additionally has the advantageous properties that it has a ROS-neutralizing effect and that it is not cleaved by the plaque bacteria in the human mouth, which is why no teeth-damaging acids are produced in the mouth when isomaltulose is consumed.

The combination of isomaltulose with galactose, which is likewise friendlier to teeth than sucrose, lends the beverage according to the invention the further advantage that it is also particularly suitable for children and teenagers, because teenagers and children prefer sweet beverages and should also protect their teeth, which are still developing in part, against caries, particularly during this development phase.

Tagatose is a naturally occurring monosaccharide, which can also be produced from galactose by means of isomerization. Tagatose has a low glycemic index of GI=3 and a sweetness of approximately 97% based on sucrose, but has a much lower energy content than sucrose because it is digested directly by the human body only to an extent of approximately 20%. The remaining 80% of the tagatose are broken down by the intestinal flora, wherein butyrate is formed inter alia and has an inhibitory effect on the growth of cancer cells, can trigger apoptosis in cancer cells and controls the sugar metabolism in cancer cells (Int J Cancer. 2010 Aug. 16. Butyrate elicits a metabolic switch in human colon cancer cells by targeting the pyruvate dehydrogenase complex.) Fructose and tagatose are known in the prior art for the fact that they suppress the formation of reactive oxygen species ("ROS") or what are known as oxygen radicals or neutralize produced oxygen radicals/ROS (Free Radic Biol Med. 1997; 22(1-2):257-268: Fructose and tagatose protect against oxidative cell injury by iron chelation) and thus counteract a possible ROS formation by galactose.

Trehalose is a natural tooth-friendly double sugar formed from two glucose molecules (alpha 1-1 bond). Its sweetness is approximately 50% of the sweetness of sucrose. The glycemic index of trehalose is approximately as high as that of isomaltulose (GI=32). Just like isomaltulose, trehalose is broken down first in the human small intestine and then causes a low insulin output. Trehalose is a non-reducing sugar and consequently does not react with free amino groups of amino acids, whereby foodstuffs containing trehalose are more stable. Since trehalose does not react with other foodstuff components due to its non-reducing properties, both these other foodstuff contents and trehalose itself are not chemically modified and are therefore available in unaltered biologically effective form. Since only glucose is released as trehalose is broken down, trehalose can also be used as a sweetening agent in the case of fructose intolerance. Trehalose lends foodstuffs a pleasant mouth sensation. In addition, trehalose suppresses flavors that are considered to be rather unpleasant by many individuals, such as a slightly bitter taste. This is accompanied by the advantage that health-promoting, yet unpleasantly tasting ingredients, such as secondary plant substances and tocotrienols can nevertheless be added in higher concentration to refreshing beverages containing trehalose.

Ribose is present in all plant and animal cells. In the animal body D-ribose is used inter alia to form adenosine triphosphate (ATP), the most important energy supplier of the metabolism. In sporting circles, D-ribose is used as a dietary supplement in order to more quickly reproduce ATP consumed during muscle activity and to therefore reduce the regeneration phase between training units. D-ribose, similarly to galactose, is metabolized completely differently compared to sucrose and its intake does not cause a rise, but rather a reduction, of the blood sugar level. Ribose therefore even has a negative glycemic index because the blood sugar level is lowered after the consumption of ribose. This can be utilized in order to lower the glycemic index of the refreshing beverage. The sweetness of ribose is approximately 30% of the sweetness of sucrose.

The gluconic acid in the beverage causes the fresh, slightly acidic taste thereof, that is to say it acts similarly to phosphoric acid, but without causing the disadvantages known for phosphoric acid. Gluconic acid, which is an organic, mild acid, is a natural product of the carbohydrate metabolism in the human body and can be produced on the basis of biotechnology from glucose (grape sugar) with the aid of microorganisms or enzymes. In contrast to phosphoric acid, the human metabolism can provide energy slowly and constantly from gluconic acid for anabolic and catabolic reactions. By contrast, phosphoric acid does not provide energy, damages the body due to the strong acid properties, and additionally stresses the mineral balance of the body since the quantity of phosphate received via phosphoric acid has to be eliminated again from the body. By contrast, gluconic acid in the human body is broken down completely into water and carbon dioxide and does not stress the mineral balance of the body, since it contains no minerals. In the state of nutritional science, gluconic acid is classified as posing no risk to health.

The combination of galactose with isomaltulose and/or tagatose and/or trehalose and/or ribose as sugar component lends the novel beverage the advantageous property that it tastes sweet, but only causes a relatively low insulin output in the human metabolism after consumption. The low insulin output provokes increased fat burning and increased activity of the mitochondria, which is very advantageous in particular for overweight individuals. The sugar combination according to the invention additionally has the advantage that it develops an inhibitory effect on the growth of cancerous ulcers, in particular of TKTL1-positive cancerous ulcers, without, at the same time, triggering cell-damaging effects in healthy cells, and also has the advantage that it increases the effect of radiation therapies and chemotherapies when fighting cancer due to the provoked activity of the mitochondria.

The risk of developing type 2 diabetes, metabolic syndrome and also high blood pressure can be lowered by a fluid supply in the form of the beverage according to the invention, in particular when the previously consumed conventional beverages of comparable taste are replaced completely or practically completely by the beverage according to the invention in order to satisfy the daily fluid need. At the same time, the beverage according to the invention is suitable as a beverage component in dietetic therapies for fighting cancerous ulcers, in particular TKTL1-positive tumors and/or metastases, wherein these dietetic therapies are based on the principle that carbohydrates which can be converted easily and quickly in the metabolism into glucose are drastically reduced.

In a preferred embodiment, the beverage according to the invention additionally has a content of fruit juices or fruit juice extracts.

In order to observe the maximum upper limit for the sugar content of the beverage in spite of the added fruit juices or fruit juice extracts, some of the sugar contained in these fruit juices or fruit juice extracts can be converted into gluconic acid by fermentation.

In a preferred variant, a content of *Stevia* is additionally provided. *Stevia* (synonyms: sweetleaf, sweet leaf and sugar leaf) is the generally conventional abbreviated name for *Stevia rebaudiana bertoni* (genus: *Stevien*, family: asteraceae). The leaves of these plants contain the diterpene glycoside stevioside, which has up to 300 times the sweetness of sugar, protects the teeth against caries and does not influence the insulin level. The dried leaves or the industrially obtained sweet extracts or derivatives thereof are used for sweetening purposes. This variant of the beverage is particularly suitable and intended for children due to its pronounced sweet taste and the protection against caries.

In a further embodiment of the beverage according to the invention, which is intended in particular for cola lovers, the beverage has content of caramel coloring and a content of natural flavorings and has a cola-like taste.

The flavorings are preferably extracts from *Mentha arvensis* and/or coca leaf and/or galangal and/or ginger and/or cardamom and/or kola nut and/or cocoa and/or lime and/or mace and/or clove and/or orange and/or pine and/or mustard seed and/or licorice and/or vanilla and/or lemon and/or cinnamon.

In a further preferred embodiment, the beverage additionally has a content of vitamin B1 in the form of the thiamine derivative benfotiamine Benfotiamine suppresses the ROS formation in cells and therefore counteracts a possible ROS formation by galactose (Diabetes Metab Res Rev. 2008 July-August; 24(5):371-7—Benfotiamine exhibits direct antioxidative capacity and prevents induction of DNA damage in vitro). In addition, benfotiamine has much better biological efficacy than thiamine and in particular causes acceleration of the degradation and conversion of the sugars contained in the beverage and a reduction or avoidance of the negative effects of sugars (advanced glucose endproducts=AGE), in particular the chronic diabetes damages.

The beverage according to the invention may additionally have a content of vitamin E in the form of a tocotrienol-tocopherol mixture from natural sources.

Vitamin E in the form of the alpha-tocopherol is known in the prior art for the fact that it very effectively suppresses the formation of reactive oxygen species ("ROS") or what are known as oxygen radicals or neutralizes produced oxygen radicals/ROS (Diabetes. 1996 September; 45(9):1233-7. Abnormalities of retinal metabolism in diabetes or experimental galactosemia. III. Effects of antioxidants; Free Radic Res. 2000 January; 32(1):67-74. Diabetes-induced metabolic abnormalities in myocardium: effect of antioxidant therapy.) Any cell-damaging effect of the monosaccharide galactose is prevented or compensated for by the combined simultaneous intake of vitamin E in the form of the natural tocotrienol-tocopherol mixture.

The tocotrienol-tocopherol mixture also has the advantage that its tocotrienols, in particular the gamma-tocotrienol and the delta-tocotrienol, in accordance with earlier research results, act in various types of cancer as inhibitors of cell proliferation and as triggers of apoptosis and therefore have a direct anti-cancer effect (for example Pharmacology. 2010; 85(4):248-58; BMC Cancer. 2010 Mar. 8; 10:84; Breast Cancer Res Treat. 2010 Feb. 16).

In particular, palm oil and rice bran or tocopherol-tocotrienol extracts from palm oil and rice bran are possible sources for the tocotrienol-tocopherol mixture.

In a further variant, the beverage additionally has a content of omega-3 fatty acids and/or medium-chain triglycerides ("MCTs"), whereby its health-promoting effect is further improved.

The omega-3 fatty acids are preferably present in the form of oilseeds. "Oilseeds" are plant seeds that can be used to obtain vegetable oils. Oilseeds include, inter alia soya, rapeseed, hemp, flax and walnut. The seeds can be used in whole form or as oil meal. "Oil meal" denotes the by-products obtained besides the oil during the processing of oilseeds and oleiferous fruits. Depending on the processing method, oil meal is also referred to as press cake (when hot-pressing or cold-pressing the oilseeds) or extraction meal (with oil extraction by solvent). Oilseeds are characterized by a high content of essential unsaturated fatty acids and essential amino acids, and additionally also contain minerals, such as magnesium, selenium or zinc. A direct anti-cancer effect has been described for some oilseeds, and such oilseeds or the corresponding oils are therefore preferably used.

MCTs promote the provision of ketone bodies and of free medium-chain fatty acids, which both have an important role in the energy metabolism, in particular as an alternative energy source to blood sugar in cancer patients with increased activity of the TKTL1 gene in the energy metabolism of healthy tissue and also in individuals with insulin resistance in the energy metabolism particularly of the nerve cells in the brain (due to their ability to pass through the blood-brain barrier).

In accordance with the invention, medium-chain triglycerides are triglycerides having a chain length of preferably C8 and/or C10.

The beverage may also have an additional content of secondary plant substances ("SPS") and may preferably contain one or more members of the following group: glucosinolates, carotenoids, lectins, flavonoids, phytosterols, polyphenols, in particular curcumin, ellagic acid, quercetin, resveratrol, delphinidin, diallyl sulfide, epigallocatechin-3-gallate, genistein, indol-3-carbinol, isoterpene, limonene, lycopene, OPC, salvestrol, and sulforaphane.

According to more recent findings, secondary plant substances have a significant efficacy, in particular in the case of chronic inflammation and mitochondrial damage and also in the case of oncological disorders. In order to achieve this effect, the secondary plant substances should not be administered or added to a foodstuff in isolated or nature-identical form, but should be taken or added to the foodstuff, that is to say in this instance the beverage according to the invention, in the form of their natural sources, preferably in the form of extracts from these natural sources The beverage may also have an additional content of $CO_2$-extracted flavorings, in particular from raspberry and/or kiwi and/or rose hip and/or ginger and/or elder and/or lychee. In contrast to the oils produced by means of conventional oil milling, $CO_2$ extracts have no metal particles from the mechanical abrasion of the oil milling process, but instead to some extent much higher concentrations of secondary plant substances.

The beverage may also have an additional content of vitamin D in order to prevent or counteract a vitamin D deficiency, since vitamin D deficiency promotes insulin resistance and metabolic syndrome, and in order to utilize the known strong anti-cancer effect of vitamin D.

In order to increase mitochondrial energy production and fat burning and to simultaneously inhibit the undesirable fermentation in cancer cells, the beverage may additionally have a content of carnitine and/or creatine.

In an embodiment in which the beverage conveys a particularly tangy and refreshing sensation when drunk, said beverage additionally has a content of carbon dioxide.

In order to meet the consumer's need for a stimulating beverage, a variant is provided in which the beverage has a content of caffeine and/or of an extract containing caffeine. Caffeine is preferably added to the beverage in the form of extracts from natural sources, such as guarana, because the caffeine is then released in this form during the digestion process in the body and therefore over a relatively long period of time and is not present as a free, directly available caffeine.

The composition of the beverage according to the invention is preferably based entirely on natural ingredients, which, in addition to the above-mentioned properties, also leads to improved tolerance and acceptance in the targeted public.

The beverage according to the invention will be explained in greater detail hereinafter with reference to formulation examples.

The quantities specified in the formulations are applicable per 100 milliliters of beverage.

EXAMPLE 1: REFRESHING BEVERAGE—LOW IN MINERALS

Ingredients:
0.4% gluconic acid
1 g galactose
0.4 g isomaltulose
0.9 g tagatose
1% chokeberry juice—partly fermented into gluconic acid

EXAMPLE 2: REFRESHING FRUIT JUICE BEVERAGE, BLACKCURRANT

Ingredients:
0.3% gluconic acid
0.9 g galactose
0.3 g isomaltulose
1 g tagatose
0.7% chokeberry juice—partly fermented into gluconic acid
0.6% blackcurrant juice—partly fermented into gluconic acid

EXAMPLE 3: REFRESHING FRUIT JUICE BEVERAGE, MIXED FRUITS

Ingredients:
0.6% gluconic acid
0.8 g galactose
0.2 g isomaltulose
1.0 g tagatose
0.3% blackcurrant juice—partly fermented into gluconic acid
0.3% cherry juice—partly fermented into gluconic acid
0.3% pear juice—partly fermented into gluconic acid
0.05% $CO_2$ ginger extract (lemon flavor)
carbon dioxide

EXAMPLE 4: REFRESHING FRUIT JUICE BEVERAGE, GINGER AND ORANGE

Ingredients:
0.3% gluconic acid
0.5 g galactose
0.2 g isomaltulose
1.5 g tagatose
1% orange juice—partly fermented into gluconic acid
0.05% $CO_2$ ginger extract (lemon flavor)
1% MCT
carbon dioxide

EXAMPLE 5: REFRESHING FRUIT JUICE BEVERAGE, RASPBERRY AND BLACKCURRANT I

Ingredients:
1.3% gluconic acid
0.7 g galactose
0.3 g isomaltulose
2.3% chokeberry juice—partly fermented into gluconic acid
2.3% blackcurrant juice—partly fermented into gluconic acid
0.05% $CO_2$ raspberry extract (rich in omega-3 fatty acids)
1.2% MCT
carbon dioxide

EXAMPLE 6: REFRESHING FRUIT JUICE BEVERAGE, RASPBERRY AND BLACKCURRANT II

Ingredients:
1.3% gluconic acid
0.7 g galactose
0.3 g isomaltulose
1.2% tagatose
0.3% chokeberry juice—partly fermented into gluconic acid
0.3% blackcurrant juice—partly fermented into gluconic acid
0.05% $CO_2$ raspberry extract (rich in omega-3 fatty acids)
1.2% MCT
0.5% natural flavors from *Mentha arvensis* and galangal and ginger and cardamom and kola nut and lime and mace and clove and orange and pine and mustard seed and licorice and vanilla and lemon and cinnamon
carbon dioxide

EXAMPLE 7: COLA BEVERAGE I

Ingredients:
2.5% gluconic acid
0.6 g galactose
0.3 g isomaltulose
1.3% tagatose
3% caramel flavoring
0.5% natural flavors from *Mentha arvensis* and galangal and ginger and cardamom and kola nut and lime and mace and clove and orange and pine and mustard seed and licorice and vanilla and lemon and cinnamon
carbon dioxide

EXAMPLE 8: COLA BEVERAGE II

Ingredients:
2.5% gluconic acid
0.8 g galactose
0.3 g isomaltulose
1.3% tagatose
3% caramel flavoring
0.5% natural flavors from *Mentha arvensis* and galangal and ginger and cardamom and kola nut and lime and mace and clove and orange and pine and mustard seed and licorice and vanilla and lemon and cinnamon
0.2% *Stevia*
carbon dioxide

EXAMPLE 9: COLA BEVERAGE III

Ingredients:
2.5% gluconic acid
0.7 g galactose
0.4 g isomaltulose
1.3% tagatose
3% caramel flavoring
0.5% natural flavors from *Mentha arvensis* and galangal and ginger and cardamom and kola nut and lime and mace and clove and orange and pine and mustard seed and licorice and vanilla and lemon and cinnamon
0.2% *Stevia*
5 mg benfotiamine
carbon dioxide

EXAMPLE 10: COLA BEVERAGE IV

Ingredients:
2.5% gluconic acid
0.7 g galactose
0.3 g isomaltulose
1.3% tagatose
3% caramel flavoring
0.5% natural flavors from *Mentha arvensis* and galangal and ginger and cardamom and kola nut and lime and mace and clove and orange and pine and mustard seed and licorice and vanilla and lemon and cinnamon
0.2% *Stevia*
5 mg benfotiamine
1% MCT
carbon dioxide

EXAMPLE 11: COLA BEVERAGE V

Ingredients:
2.5% gluconic acid
0.8 g galactose
0.4 g isomaltulose
1.1% tagatose
1.8% caramel flavoring
0.5% natural flavors from *Mentha arvensis* and galangal and ginger and cardamom and kola nut and lime and mace and clove and orange and pine and mustard seed and licorice and vanilla and lemon and cinnamon
0.2% *Stevia*
15 mg benfotiamine
25 mg carnitine
65 mg creatine
2% MCT
carbon dioxide

EXAMPLE 12: COLA BEVERAGE VI

Ingredients:
0.5% gluconic acid
0.3 g galactose
0.6% trehalose
0.4 g isomaltulose
0.6% tagatose
0.1% ribose
1.0 g erythritol
0.8% caramel flavoring
0.5% natural flavors from *Mentha arvensis* and galangal and ginger and cardamom and kola nut and lime and mace and clove and orange and pine and mustard seed and licorice and vanilla and lemon and cinnamon
0.2% *Stevia*
15 mg benfotiamine
25 mg carnitine
65 mg creatine
2% MCT
carbon dioxide

EXAMPLE 13: COLA BEVERAGE VII

Ingredients:
0.5% gluconic acid
0.5 g galactose
0.6% trehalose
0.4 g isomaltulose
0.6% tagatose
0.1% ribose
1.0 g erythritol
0.7% caramel flavoring
0.5% natural flavors from *Mentha arvensis* and galangal and ginger and cardamom and kola nut and lime and mace and clove and orange and pine and mustard seed and licorice and vanilla and lemon and cinnamon
0.2% *Stevia*
15 mg benfotiamine
25 mg carnitine
65 mg creatine
2% MCT
carbon dioxide

EXAMPLE 14: REFRESHING FRUIT JUICE BEVERAGE, GOJI, BLACKCURRANT AND ORANGE FLAVOR

Ingredients:
0.5% gluconic acid
0.5 g galactose
0.7% trehalose
0.4 g isomaltulose
0.6% tagatose
0.1% ribose
1.0 g erythritol
0.2% *Stevia*
0.1% goji juice
0.3% blackcurrant—partly fermented into gluconic acid
0.01% natural orange flavor
15 mg benfotiamine
25 mg carnitine
65 mg creatine
2% MCT
carbon dioxide

EXAMPLE 15: REFRESHING BEVERAGE, LOW IN MINERALS

Ingredients:
0.4% gluconic acid
0.5 g galactose
0.8% trehalose
0.4 g isomaltulose
0.1% ribose
0.4 g tagatose
0.6% chokeberry juice—partly fermented into gluconic acid
0.3% *Stevia*

The invention claimed is:
1. A method of administering a beverage that is free from phosphoric acid to an individual in need thereof comprising:
   providing a beverage comprising:
   water;
   at least 0.3 wt/vol % gluconic acid;
   less than 0.025 wt/vol % minerals; and
   not more than 2.5 wt/vol % sugars, said sugars comprising:
      galactose in the form of a monosaccharide and wherein the galactose constitutes at least 10 wt/wt % of sugars in the beverage; and
      tagatose in the form of a monosaccharide and/or isomaltulose in an amount effective to counteract formation of reactive oxygen species by the galactose, and wherein the beverage has a glycemic index that does not exceed 35 (GI<35) and is free from phosphoric acid; and
   administering the beverage to said individual.

2. The method of claim 1, wherein the beverage comprises less than 0.015 wt/vol % minerals.

3. The method of claim 1, wherein the beverage further comprises fruit juices or fruit juice extracts.

4. The method of claim 1, wherein the beverage further comprises stevia.

5. The method of claim 1, wherein the beverage further comprises caramel coloring.

6. The method of claim 5, further comprising flavorings selected from the group consisting of *mentha arvensis*, coca leaf, galangal, ginger, cardamom, kola nut, cocoa, lime, mace, clove, orange, pine, mustard seed, licorice, vanilla, lemon, cinnamon, extracts thereof and combinations thereof.

7. The method of claim 1, wherein the beverage further comprises benfotiamine.

8. The method of claim 1, wherein the beverage further comprises a tocotrienol-tocopherol mixture.

9. The method of claim 1, wherein the beverage further comprises omega-3 fatty acids and/or medium-chain triglycerides ("MCTs").

10. The method of claim 1, wherein the beverage further additionally comprises secondary plant substances, which are selected from the group consisting of glucosinolates, carotenoids, lectins, flavonoids, phytosterols, polyphenols, in particular curcumin, ellagic acid, quercetin, resveratrol, delphinidin, diallyl sulfide, epigallocatechin-3-gallate, genistein, indol-3-carbinol, isoterpene, limonene, lycopene, OPC (oligomeric proanthocyanidin), salvestrol, sulforaphane and ubiquinone.

11. The method of claim 1, wherein the beverage further comprises $CO_2$-extracted flavors.

12. The method of claim 1, wherein the beverage further comprises vitamin D.

13. The method of claim 1, wherein the beverage further comprises carnitine and/or creatine.

14. The method of claim 1, wherein the beverage contains carbon dioxide.

15. The method of claim 1, wherein the beverage further comprises caffeine or at least one extract containing caffeine.

16. The method of claim 1, wherein the beverage is free from artificial sweeteners, artificial colorants and artificial flavorings.

17. The method of claim 1, further comprising trehalose and/or ribose.

18. The method of claim 1, wherein the individual suffers from an illness benefiting from a beverage that is free from phosphonic acid.

19. The method of claim 18, wherein the illness is Alzheimer's disease.

20. The method of claim 1, wherein the beverage comprises less than 0.01 wt/vol % of minerals.

* * * * *